United States Patent [19]

Akatsu et al.

[11] Patent Number: 5,068,481

[45] Date of Patent: Nov. 26, 1991

[54] METHOD FOR PRODUCING DIARYLMETHANES

[75] Inventors: Masahiro Akatsu; Hajime Takayama; Takeshi Matsuoka, all of Iwaki, Japan

[73] Assignee: Kureha Kagaku Kogyo K.K., Japan

[21] Appl. No.: 611,589

[22] Filed: Nov. 13, 1990

[30] Foreign Application Priority Data

Nov. 16, 1989 [JP] Japan .................... 1-296142

[51] Int. Cl.$^5$ .............................. C07C 2/02
[52] U.S. Cl. ......................... 585/426; 585/428; 585/429
[58] Field of Search ............ 585/426, 428, 429

[56] References Cited

U.S. PATENT DOCUMENTS 2,850,545  9/1958  Fetterly et al. ............ 585/426
3,109,868  11/1963 Fields et al. ............... 585/426
3,799,991  3/1974  Smith ........................ 585/426

FOREIGN PATENT DOCUMENTS 2542133  3/1984  France .
49-31652  3/1974  Japan .
60-87231  5/1985  Japan .
61-27930  2/1986  Japan .
64-31734  2/1989  Japan .

Primary Examiner—Patrick P. Garvin
Assistant Examiner—E. D. Irzinski
Attorney, Agent, or Firm—Lowe, Price LeBlanc & Becker

[57] ABSTRACT

The present invention relates to a method for producing diarylmethanes represented by the following formula (III)

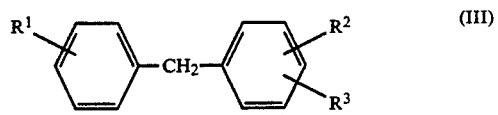

wherein $R^1$ and $R^3$ each stand for a hydrogen atom or an alkyl group having 1 to 3 carbon atoms. This method comprises the reaction of a benzyl chloride represented by the following general formula (I) with benzene or an alkylbenzene represented by the following general formula (II):

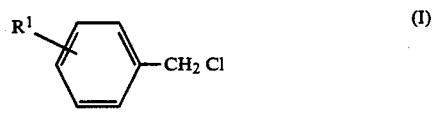

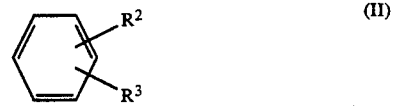

wherein $R^1$ to $R^3$ have the same meanings as defined above and is characterized in that the catalyst used is an HY or HL type zeolite having a $SiO_2/Al_2O_3$ molar ratio of 4–10 and an alkali metal content of 5% by weight or less, calculated as an alkali metal oxide, or a zeolite obtained by the exchange of said HY or HL type zeolite with cations of a di- or tri-valent metal.

5 Claims, No Drawings

METHOD FOR PRODUCING DIARYLMETHANES

BACKGROUND OF THE INVENTION

1. Field of the Invention

The present invention relates to a method for producing diarylmethanes useful as various solvents, etc.

2. Description of the Related Art

Diarylmethanes are used as carbonless copying paper solvents because of being well soluble and compatible colorformers and dyes.

Heretofore, diarylmethanes have been prepared by the condensation of an alkylbenzene with an aldehyde at a low temperature using concentrated sulfuric acid as a catalyst, as disclosed in Japanese Patent Kokai Laid-open No. 61(1986)-27930. A problem with this method, however, is that the starting aldehyde itself is so liable to be polymerized that the reaction should be carried out at a very low temperature, say, $-40$ to $-20$C., needing a cooling medium. Also, the condensate should be neutralized to remove the sulfuric acid catalyst. Thus, this condensation method is not only troublesome to handle but is also low in both conversion and selectivity. Another long-established method, in which benzyl chloride is used as raw material in the presence of a Friedel-Crafts catalyst such as aluminium chloride or iron chloride, gives large amounts of by-products such as polymers of benzyl chloride and several compounds having 3 or more benzene rings. For instance, Japanese Patent Application Laid-Open No. 60(1985)-87231 discloses that chlorine is allowed to react with toluene through a free-radical reaction mechanism and an inorganic halide or acid is then permitted to act on the resulting reaction product. Japanese Patent Application Laid-Open No. 64(1989)-31734, on the other hand, set forth that chlorine is allowed to react with toluene or xylene in the presence of a free-radical generator and, after removal of the unreacted toluene or xylene, a benzene compound having a $C_2$–$C_{16}$ hydrocarbon chain is allowed to react with the chlorinated product in the presence of an inorganic halide or acid. In the processes disclosed in both the publications, iron chloride, aluminium chloride and so on are used as the inorganic halides and concentrated sulfuric acid and zeolite as the inorganic acids. In their examples wherein only iron chloride is used, however, the yield of diarylmethanes is short of 80% or, in other words, 20% or more of six compounds having 3 or more benzene rings are formed. In still another method disclosed in French Patent No. 2543133, toluene is chlorinated to form dichlorotoluene and dichlorobenzyl chloride, which are then permitted to react with each other at 180°–199° C., using as a catalyst a cation-free X or Y type zeolite freed of cations, thereby forming tetrachloro-diphenylmethane.

As mentioned above, various methods for producing diarylmethanes from benzyl chlorides and alkylbenzenes have been known in the art. The method using the concentrated sulfuric acid or Friedel-Crafts catalysts, however, involves some problems in connection with the reaction temperature, by-products, reaction equipments and so on. The methods using the solid acid catalysts, on the other hand, have to be carried out at a reaction temperarure of at least 100° C. and is less than satisfactory in terms of selectivity.

It is thus desired to develop a method for producing diarylmethanes under more mild conditions but more increased rectivity and selectivity than so far achieved

SUMMARY OF THE INVENTION

An object of this invention, therefore, is to provide a method for producing high-selectivity diarylmethanes under mild conditions, e.g., at a low reaction temprature but in a high yield with more increased conversion and selectivity than so far achieved.

As a result of intensive studies made of how to prepare diarylmethanes with more increased conversion and selectivity than so far achieved, the inventors have accomplished the present invention.

More specially, the present invention provides a method for producing 1,1-diarylmethanes represented by the following general formula (III) by the condensation reaction of a benzyl chloride represented by the following general formula (I) with benzene or an alkylbenzene represented by the following general formula (II).

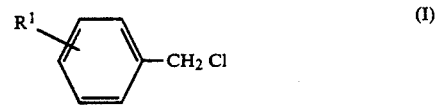 (I)

 (II)

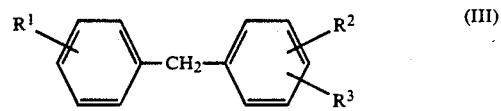 (III)

wherein $R^1$ to $R^3$ each stand for a hydrogen atom or an alkyl group having 1-3 carbon atoms, characterized in that: the catalyst used is an HY or HL type zeolite having a $SiO_2/Al_2O_3$ molar ratio of 4-10 and an alkali metal content of 5% by weight or less, calculated as an alkali metal oxide $M_2O$ wherein M stands for an alkali metal, or a zeolite obtained by the exchanging of said HY or HL type zeolite with cations of a di- or tri-valent metal.

DETAILED DESCRIPTION OF PREFERRED EMBODIMENTS

The present invention will now be explained in more details.

The benzyl chlorides used as one of the starting materials in this invention are represented by the general formula (I), and exemplified by benzyl chloride, methylbenzyl chloride, ethylbenzyl chloride and propylbenzyl chloride.

The other starting materials are benzene or alkylbenzenes which are represented by the general formula (II) and exemplified by toluene, xylene, ethylbenzene or isopropylbenzene. The compounds expressed by the general formula (II) may be used in the form of a mixture of two or more.

The catalyst used in this invention is an HY or HL type zeolite having a $SiO_2/Al_2O_3$ molar ratio of 4–10 and an alkali metal content of 5% by weight or less, calculated as an alkali metal oxide $M_2O$ wherein M stands for an alkali metal, or a zeolite obtained by the exchange of said HY or HL type zeolite with cations of a di- or tri-valent metal. A zeolite catalyst, having either the $SiO_2/Al_2O_3$ molar ratio or the alkali metal content departing from the above-defined range, is unpractical, partly because the activity is so insufficient that the reaction temperature should be increased and partly because the selectivity is so low that the amount of oligomers of benzyl chlorides and high-boiling materials such as compounds having 3 or more benzene rings are increased. Depending upon the lattice constant (Å), the HY type zeolite is classified into HY (with a lattice constant Å>24.55), HSY(with Å of 24.45 to 24.55), and USY(with Å<24.45) types, all usable in this invention.

The zeolite catalyst used in this invention, for instance, may be prepared in the following procedure. That is, a synthetic Y type zeolite having a $SiO_2/Al_2O_3$ molar ratio of 4-10 and a $Na_2O$ content of 12-14% by weight is immersed in a solution containing hydrogen ions or cations exchangeable to hydrogen ions, e.g., an aqueous solution of ammonium chloride or ammonium sulfate, wherein the ion-exchangeable Na is exchanged with hydrogen ions, thereby decreasing the content of sodium to 5% by weight or less, preferably 0.5% by weight, calculated as $Na_2O$. After washing with water, this zeolite is heated at 300°-400° C. into the HY type zeolite. If required, some hydrogen ions may be exchanged with cations of a di- or tri-valent metal such as Ca, Mg, Cu, Zn, Mn, Cr, Co or Ni or lanthanide series cations to increase the acid strength. For the introduction of the metal cations, the HY type zeolite is treated with an acidic solution (pH 1.5-5.5) of a salt of a foresaid di- or tri-valent metal and after washing with water, heated at about 400° C. in a nitrogen gas atmosphere. Such metal salts, for instance, may be copper chloride, copper sulfate, calcium chloride, zinc chloride, zinc sulfate, ammonium zinc sulfate, zinc acetate, chromium chloride, chromium sulfate, chromium nitrate, ammonium chromium sulfate, cobalt chloride, cobalt nitrate, cobalt sulfate, nickel chloride, manganese chloride, manganese sulfate and magnesium chloride.

Likewise, the L type zeolite may be converted from a synthetic L type zeolite into the HL type zeolite, into which the cations of the aforesaid di- or tri-valent metals may be introduced, if required.

In carrying out this invention, the molar ratio of the benzene or alkylbenzene to the benzyl chloride is 5 or more, preferably 7 or more. The higher the molar ratio of the two reactants, the more improved the selectivity of a diarylmethane. Thus, both the reactants should preferably be used at as high a molar ratio as possible unless it is otherwise economically unfavorable. A molar ratio less than 5 is unpreferred, because the selectivity of the end diarylmethane drops with an increase in the amount of high-boiling by-products.

The proportion of the catalyst zeolite used may be suitably determined depending upon the form of reaction. For a batchwise reaction, for instance, it may be used in an amount of 1-50% by weight, preferably 5-40% by weight with respect to the benzyl chloride. For a continuous reaction carried out especially with a fixed bed type of reactor, the proper amount of the catalyst zeolite may be determined experimentally, e.g., by an LHSV value. When a tubular flow type of reactor is used for the continuous reaction, its length (L) to diameter (D) ratio -L/D- should preferably be 5 or more.

The reaction should be carried out at a reaction temperature in the range of 20° C. to the boiling point of the reaction solution, preferably 30° to 100° C., more preferably 35° to 90° C. A reaction temperature higher than the boiling point of the reaction solution is unpreferred in view of unit process, because a high pressure has to be applied to maintain a liquid-phase reaction. A reaction temperature less than 20° C. is again unpreferred, bacause the reaction rate slows down.

According to this invention, no particular limitation is imposed upon how the reaction is carried out. If desired, the reaction may be performed either batchwise or continuously. Although depending upon how the reaction is carried out or how large the reaction scale is, the reaction time may be 0.5 to 5 hours.

It is understood that the end diarylmethane can easily be obtained with high purity by distillation from the reaction solution after the reaction.

According to this invention wherein the aforesaid zeolite catalyst is used to permit the benzyl chloride to react with the benzene or alkylbenzene to produce a diarylmthane, it is possible to carry out the reaction under mild conditions. e.g. at a reaction temperature lower than the boiling point of the benzene or alkylbenzene or, in most cases, at about 35°-90° C. and separate easily the end diarylmethane from the reaction solution by distillation.

According to this invention, the benzyl chloride reacts with the benzene or alkylbenzene at a high conversion, yielding the diarylmethane at a high selectivity. The present invention gives the diarylmethane in a yield of 90% or higher and reduces the formation of high-boiling materials by side reactions much more than achieved by conventional methods.

EXAMPLES

The present invention will now be explained more specifically but not exclusively with reference to the following examples.

EXAMPLE 1

The catalyst used was a commercially available HSY type zeolite - HSZ-331HSA made by Toso Co., Ltd. and heat-treated in a nitrogen gas atmosphere at 400° C. for 2 hours with a $SiO_2/Al_2O_3$ molar ratio of 6.6, a hydrogen ion exchange rate of 98% and a $Na_2O$ content of 0.25% by weight.

In a 500 ml separable flask equipped with a stirrer, a dropping funnel and a thermometer were placed 20 g of the aforesaid catalyst and 355.5 g (3.87 moles) of toluene. The mixture was stirred and heated at about 80° C. While the mixture was maintained at that temperature, 66.2 g (0.523 moles) of benzyl chloride were added dropwise to it through the dropping funnel over one hour. Thereafter, both the reactants were allowed to react with each other at a reaction temperature maintained at 80±2° C. for 3 hours to obtain 402.9 g of a reaction solution.

By gas chromatography analysis, the reaction solution was found to be composed of toluene, benzyl chloride, tolylphenylmethane (hereinafter abbreviated as TPM) and high-boiling materials in the concentrations shown in Table 1. The amount of TPM was 89.4 g (0.491 moles), while the amount of the high-boiling materials was 4.34 g.

Based on the compositional analysis of the reaction solution, the conversion of benzyl chloride and the selectivity and yield of TPM were calculated by the following equations:

Conversion of benzyl chloride=(Starting Amount - Unreacted Amount)/(Starting Amount)×100

Selectivity of TPM = (Amount of TPM in the Reaction Solution)/(Total Amount of TPM and High-Boiling Materials in the Reaction Solution) × 100

Yield of TPM = (Amount of TPM)/(Theoretical Yield of TPM) × 100

EXAMPLE 2

Example 1 was repeated, provided that the temperature at which benzyl chloride was added dropwise and the reaction temperature were both maintained at 40±1° C. The results are shown in Table 1.

EXAMPLE 3

The catalyst used was a commercially available USY type zeolite - TSZ-350HUA made by Toso Co., Ltd. and heat-treated in a nitrogen stream at 400° C. for 2 hours with a $SiO_2/Al_2O_3$ molar ratio of 9.2, a hydrogen ion exchange rate of 98.5% and a $Na_2O$ content of 0.29% by weight.

20 g of the aforesaid catalyst and 363.3 g (3.43 moles) of mixed xylene were put into an equipment similar to that used in Example 1, which was then heated to about 80° C. Afterwards, 58.7 g (0.464 moles) of benzyl chloride was added dropwise to the equipment through the dropping funnel over one hour. The two reactants were allowed to react with each other at a reaction temperarure maintained at 80±2° C. for 3 hours to obtain 405.1 g of a reaction solution. The reaction solution contained 82.3 g (0.420 moles) of xylylphenylmethane (hereinafter abbreviated as XPM) and 6.34 g of high-boiling materials. The composition of the reaction solution, the conversion of benzyl chloride and the selectivity of XPM were determined. The results are shown in Table 1.

EXAMPLE 4

Example 1 was repeated, provided that the catalyst used was commercially available HY type zeolite - TSZ-320HOA made by Toso Co., Ltd. and heat-treated in a nitrogen stream at 400° C. for 2 hours with a $SiO_2/Al_2O_3$ molar ratio of 5.6, a hydrogen ion exchange rate of 69% and a $Na_2O$ content of 4.36% by weight. The results are shown in Table 1.

EXAMPLE 5

Example 1 was repeated, provided that the catalyst used commercially available HL type zeolite - TSZ-500HOA made by Toso Co., Ltd. with a $SiO_2/Al_2O_3$ molar ratio of 6.3 and a $K_2O$ content of 4.5% by weight. The results are shown in Table 1.

EXAMPLE 6

Example 1 was repeated, provided that the catalyst used was an HSY type zeolite which was similar to that used in Example 1 but was exchanged with 10% calcium ions in an acidic aqueous solution of calcium chloride and further heat-treated in a nitrogen gas atmosphere at 400° C. for 2 hours. The results are shown in Example 6-1 of Table 1. The results of the catalyst exchanged with 10% cupric ions in a cupric chloride solution are also shown in Example 6-2 of Table 1.

COMPARATIVE EXAMPLE 1

Example 1 was repeated, provided that the catalyst used was commercially available NaY type zeolite - TSZ-320NAA made by Toso Co., Ltd. and heat-treated in a nitrogen gas atmosphere at 400° C. for 2 hours with a molar $SiO_2/Al_2O_3$ ratio of 5.6 and a $Na_2O$ content of 12.3% by weight. The results are shown in Table 1.

COMPARATIVE EXAMPLE 2

Example 1 was repeated, provided that the catalyst used was commercially available USY type zeolite - TSZ-360XOA made by Toso Co., Ltd. and heat-treated in a nitrogen gas atmosphere at 400° C. for 2 hours with a $SiO_2/Al_2O_3$ molar ratio of 14.5 and a $Na_2O$ content of 0.02% by weight. The results are shown in Table 1.

COMPARATIVE EXAMPLE 3

Example 1 was repeated, provided that the catalyst used was an HY type zeolite with a $SiO_2/Al_2O_3$ molar ratio of 3.5 and a $Na_2O$ content of 3.6% by weight, which was heat-treated in a nitrogen stream at 400° C. for 2 hours. The results are shown in Table 1.

COMPARATIVE EXAMPLE 4

With 10 g of an acidic Friedel-Crafts catalyst ($FeCl_3$), the two reactants were permitted to react with each other at a reaction temperature of 60° C. in the equipment of Example 1. However, the selectivity was poor, as will be understood from the results shown in Table 1.

EXAMPLE 7

A commercially available HSY type zeolite similar to that used in Example 1 was pelletized into an HSY type zeolite catalyst HSZ-331HSD having a diameter of 1.5 mm and a length of 5-10 mm, using as a pelletizing binder 15 parts by weight of alumina with respect to 100 parts by weight of anhydrous zeolite. Using this catalyst and three (tubular) flow types of reactor (having different diameters and lengths), TPMs were produced.

For the reaction, a mixture of toluene with 15.7% by weight of benzyl chloride was fed to the reactors through a constant rate pump. The reaction temperature was 30° C.

The results are reported in Table 1.

The flow type of reactors used had the following lengths (L) and diameters (D).

| Reactor | Length (L) | Diameter (D) | L/D | Amount of Catalyst packed |
|---|---|---|---|---|
| A | 180 mm | 62 mm | 2.9 | 500 mml |
| B | 330 | 62 | 5.3 | 1000 |
| C | 420 | 40 | 10.5 | 500 |

TABLE 1

|  | Example 1 | Example 2 | Example 3 | Example 4 | Example 5 | Example 6-1 |
|---|---|---|---|---|---|---|
| Type of Catalyst | HSY | HSY | USY | HY | HL | HSY |
| $H^+$ ion exchange | 98% | 98% | 98.5% | 69% | 74% | 98% |
| Metal cation exchange | — | — | — | — | — | Ca 10% |
| $SiO_2/Al_2O_3$ | 6.6 | 6.6 | 9.2 | 5.6 | 6.3 | 6.6 |
| $Na_2O$ | 0.29 wt % | 0.29 wt % | 0.25 wt % | 4.36 wt % | — | 0.29 wt % |
| $K_2O$ | — | — | — | — | 4.5 wt % | — |
| Trade name of catalyst | HSZ-331HSA | HSZ-331HSA | TSZ-350HUA | TSZ-320HOA | TSZ-500HOA | — |
| Starting molar ratio | 1/7.39 | 1/7.39 | 1/7.39 | 1/7.39 | 1/7.39 | 1/7.39 |

TABLE 1-continued

| | | | | | | |
|---|---|---|---|---|---|---|
| Reaction temperature | 80° C. | 40° C. | 80° C. | 80° C. | 80° C. | 80° C. |
| Composition of reaction solution | | | | | | |
| Toluene | 76.73 wt % | 77.40 wt % | — | 76.68 wt % | 77.99 wt % | 76.44 wt % |
| Xylene | — | — | 78.13 wt % | — | — | — |
| Benzyl chloride | 0.00 | 1.88 | 0.00 | 0.03 | 3.07 | 0.00 |
| TPM | 22.20 | 20.49 | — | 22.39 | 18.72 | 23.33 |
| XPM | — | — | 20.31 | — | — | — |
| High-boiling materials | 1.07 | 0.24 | 1.56 | 0.90 | 0.21 | 0.23 |
| Conversion | 100 | 88.52 | 100 | 99.83 | 81.12 | 100 |
| Selectivity | 95.37 | 98.83 | 92.85 | 96.13 | 98.86 | 99.03 |
| Yield | 93.90 | 98.43 | 90.44 | 94.89 | 98.48 | 98.70 |

| | Example 6-2 | Comparative Example 1 | Comparative Example 2 | Comparative Example 3 | Comparative Example 4 |
|---|---|---|---|---|---|
| Type of Catalyst | HSY | NaY | USY | HY | Ferric chloride |
| H$^+$ ion exchange | 98% | 12% | 99.9% | 75% | — |
| Metal cation exchange | Cu 10% | — | — | — | — |
| SiO$_2$/Al$_2$O$_3$ | 6.6 | 5.6 | 14.5 | 3.5 | — |
| Na$_2$O | 0.29 wt % | 12.3 wt % | 0.02 wt % | 3.6 wt % | — |
| K$_2$O | — | — | — | — | — |
| Trade name of catalyst | — | TSZ-320NAA | TSZ-360XOA | — | — |
| Starting molar ratio | 1/7.39 | 1/7.39 | 1/7.39 | 1/7.39 | 1/7.39 |
| Reaction temperature | 80° C. | 80° C. | 80° C. | 80° C. | 80° C. |
| Composition of reaction solution | | | | | |
| Toluene | 76.50 wt % | 79.87 wt % | 84.31 wt % | 79.58 wt % | 78.21 wt % |
| Xylene | — | — | — | — | — |
| Benzyl chloride | 0.00 | 5.03 | 15.69 | 4.48 | 0.32 |
| TPM | 23.09 | 12.23 | 0.00 | 13.16 | 16.51 |
| XPM | — | — | — | — | — |
| High-boiling materials | 0.41 | 2.87 | 0.00 | 2.78 | 4.96 |
| Conversion | 100 | 68.96 | 0.00 | 72.36 | 98.03 |
| Selectivity | 98.25 | 81.02 | 0.00 | 82.53 | 76.88 |
| Yield | 97.66 | 76.13 | 0.00 | 77.92 | 71.30 |

What is claimed is:

1. In a method for producing diarylmethanes represented by the following general formula (III) by the reaction of a benzyl chloride represented by the following general formula (I) with benzene or an alkylbenzene represented by the following general formula (II):

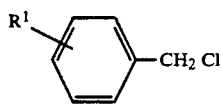 (I)

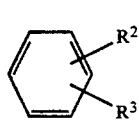 (II)

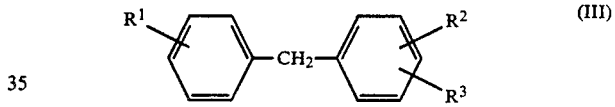 (III)

wherein R$^1$ to R$^3$ each stand for a hydrogen atom or an alkyl group having 1 to 3 carbon atoms, the improvement comprising that the catalyst used is an HY or HL type zeolite having a SiO$_2$/Al$_2$O$_3$ molar ratio of 4 to 10 and an alkali metal content of 5% by weight or less, calculated as an alkali metal oxide, or a zeolite obtained by exchanging said HY or HL type zeolite with cations of a di- or tri-valent metal.

2. A method as claimed in claim 1, wherein the diarylmethane is tolylphenylmethane.

3. A method as claimed in claim 1, wherein the diarylmethane is xylylphenylmethane.

4. A method as claimed in claim 1, wherein the cations of a di- or tri-valent metal are those of a metal selected from the group consisting of Ca, Mg, Cr, Mn, Ni, Zn and Cu.

5. A method as claimed in claim 1, wherein the molar ratio of the alkylbenzene to benzyl chloride is 5 or more.

* * * * *